US00PP07825P

United States Patent [19]

Fruehwirth

[11] Patent Number: Plant 7,825

[45] Date of Patent: Mar. 10, 1992

[54] POINSETTIA PLANT '490'

[75] Inventor: Franz Fruehwirth, Encinitas, Calif.

[73] Assignee: Paul Ecke Ranch, Inc., Encinitas, Calif.

[21] Appl. No.: 528,234

[22] Filed: May 24, 1990

[51] Int. Cl.[5] ..... A01H 5/00

[52] U.S. Cl. ..... Plt./86

[58] Field of Search ..... Plt./86, 86.4

[56] References Cited

U.S. PATENT DOCUMENTS

P.P. 5,150 11/1983 Ecke, Jr. ..... Plt. 86

4,724,276 2/1988 Ecke, Jr. ..... 47/58

*Primary Examiner*—Howard J. Locker

*Attorney, Agent, or Firm*—Arnold, White & Durkee

[57] ABSTRACT

Poinsettia '490' is a very early flowering cultivar with dark red flower bracts. It has dark green, medium size foliage and a strong branching habit. The stem length is relatively short and chemical growth retardants may not be needed to control the height of flowering plants. Because of its early flowering '490' can be grown for an early market under natural daylength conditions.

1 Drawing Sheet

BACKGROUND OF THE NEW PLANT

This new Poinsettia cultivar '490' originated as an induced sport of a seedling Poinsettia known as 'C-17' from cross pollination (not patented) in my greenhouse in Encinitas, Calif. '490' is self-branching, whereas 'C-17' is not a self-branching cultivar. It was selected because of its early flowering, short stature, dark red flower bracts, dark green foliage and strong branching habit; traits which distinguish it from other Poinsettia cultivars, such as 'R-13' and seem to make it a desirable plant for commercial greenhouse production. Although 'R-13' has dark red bracts and dark green foliage, cultivar '490' is shorter, more compact with shorter internodes, requires less growth retarding chemicals for commercial production, typically has 5–6 more flower bracts, and flowers 10 days earlier than 'R-13'. Additionally, cultivar '490' has self-branching traits, whereas 'R-13' does not. After selection, stem cuttings of this plant were vegetatively reproduced for test purposes in Encinitas, Calif., and clones of this plant were subjected to successive generations of vegetative propagation which demonstrated that its distinctive characteristics hold true from generation to generation.

DESCRIPTION OF THE PHOTOGRAPHS

Poinsettia '490' is illustrated in the accompanying color photographs. The upper photo is a side view of 3 single stem plants per pot in full flower. Evidence of self branching can be seen in the flowering axillary branches beneath the upper canopy of bracts. The lower photo is a top view of the same plant showing flower and bract formation.

DESCRIPTION OF THE PLANT

The following is a detailed description of this new Poinsettia '490' as observed in my greenhouse in Encinitas, Calif., during December 1989. Observations were recorded from flowering plants, grown as 3 unpinched plants per pot. The pot was 14 cm. in diameter and 11 cm. in height. Comparisons were made under the same cultural conditions to cultivar 'C-17' from which '490' is derived, and to cultivar 'R-13' (U.S. Plant Pat. No. 5,510) which has similar bract and foliage colors. Color designations are compared to the 1986 edition of R.H.S. Colour Chart, first published in 1966 by The Royal Horticultural Society, London, England.

The Plant

Origin: Sport of a seedling. The sport was induced by application of the procedures set forth in U.S. Pat. No. 4,724,276 to the seedling parent.

Classification:

*Botanic.*—*Euphorbia pulcherrima* Willd.

*Common name.*—Poinsettia.

*Cultivar name.*—'490'.

Form: Shrub.

Height: Short.

Growth habit: As a single stemmed plant, upright and short. The application of a chemical growth retardant may not be needed to restrict height for commercial pot plant production. I observed 3 plants in a pot with an overall height of 43 cm. and an overall width of 48 cm. By contrast, overall heights of 'C-17' and 'R-13' were 45 cm. and 53 cm., respectively. The bract diameter of individual flowers was 30 cm.

Branching: Poinsettia '490' has self-branching traits. Axillary branches will develop and terminate in a flower without pinching. Neither 'C-17' nor 'R-13' have self-branching traits. It may be desirable to pinch '490' and remove all terminal dominance. Then, 6–8 axillary branches usually will develop uniformly and at a faster rate. Even after pinching, only 4–5 axillary branches develop on 'C-17' and only 3–4 branches on 'R-13'. The branching of '490' and 'C-17' is mostly unaffected by warm cultural conditions, whereas the branching of 'R-13' is often reduced in warmer climates.

Growth rate: Rooting of stem cuttings occurs in 12–18 days under intermittent mist. The plant will flower in about eight weeks under continuous long night conditions and night temperatures of about 16–18 degrees C. Plants of '490' and 'C-17' were in "full flower" on November 22, ten days earlier than 'R-13' which flowered on December 2.

Foliage: The foliage is clean and uniformly dark green from bottom to top of the plant. The leaves are of medium size, leaf blades typically being about 13–15 cm. long and about 10–11 cm. wide with leaf petioles about 6–7 cm. long. Leaves of '490' and 'C-17' are longer in relation to their width than leaves of 'R-13'.

*Leaf shape.*—Typical leaves are ovate with obtuse bases and acuminate tips. Leaf margins are usually entire with a few leaves slightly lobed with one small indentation on one or both sides of the leaf blade.

*Color.*—Upper side — Dark green, much darker than R.H.S. 139A. Under side — Green, between R.H.S. 147A and R.H.S. 147B.

*Retention.*—The foliage lasts extremely well even under low light intensities in the consumer's home.

Bracts: Generally there are 18–24 uniformly colored bracts of various sizes subtending the cyathia. Inflorescences of '490' and 'C-17' averaged 22 bracts compared to 16 for 'R-13'. The primary bracts have blades typically 16–18 cm. long and 9–11 cm. wide with petioles about 4 cm. long.

*Shape.*—Primary bracts are mostly ovate with acute bases and acuminate tips. Secondary bracts are elliptic. Primary bracts are lobed with 1 or 2 indentations on either side of the bracts. Secondary bracts have entire margins. Bracts of '490' and 'C-17' are longer relative to their width than bracts of 'R-13'.

*Color.*—Upper side — Dark red, near R.H.S. 45A. Under side — Red, near R.H.S. 53C. The red bract color of '490' and 'C-17' is relatively brighter than 'R-13'. 'R-13' bracts have a more bluish tone.

Flowers: Generally, 15–21 cyathia (flowers) are present when the plant is in full bloom. Each cyathium is about 8 mm long and about 6 mm wide, green in color, and fringed with red at the distal end. Usually one yellow nectar cup protrudes from the side of each cyathium. The flower pedicel is also green and about 5–6 mm in length. The stamens protruding from the cyathia are red.

What is claimed is:

1. A new and distinct Poinsettia cultivar, substantially as herein shown and described, characterized by its early flowering, short stature, dark red flower bracts, dark green foliage and strong branching habit.

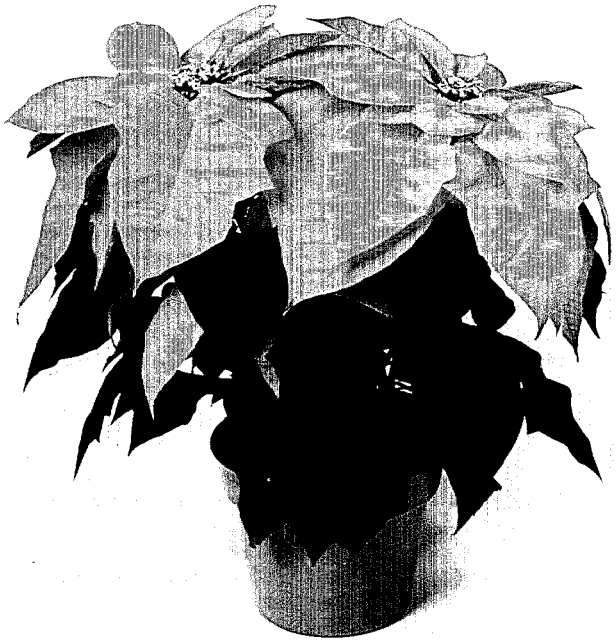
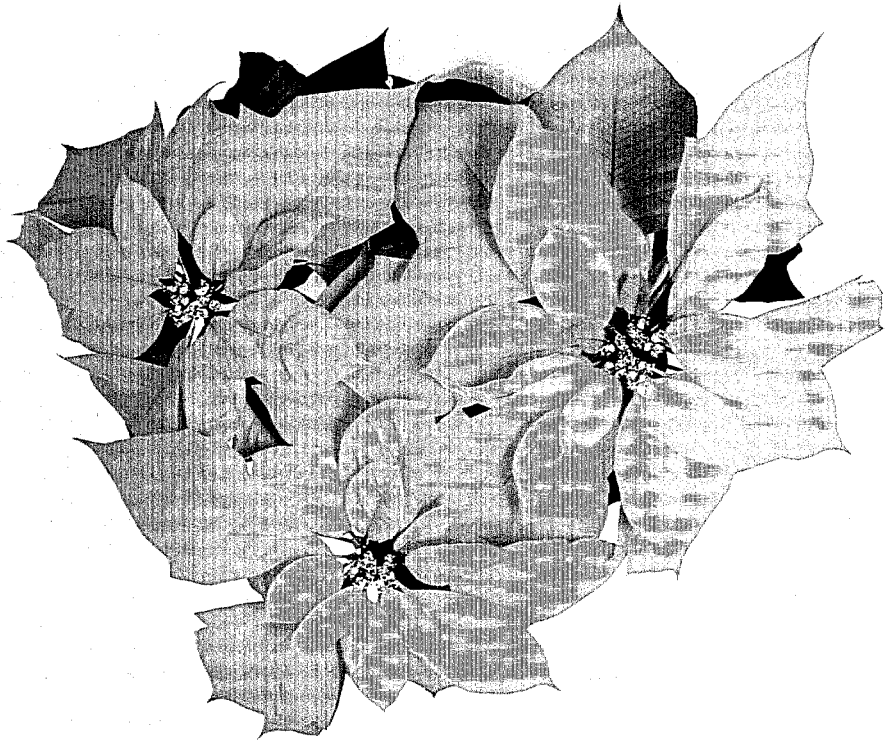

* * * * *